United States Patent [19]

Yen

[11] Patent Number: 5,716,643

[45] Date of Patent: Feb. 10, 1998

[54] LARGE SCALE PRODUCTION OF MEDICINE COATED CROSSLINKED PROTEIN MICROSPHERES

[75] Inventor: Richard C. K. Yen, Yorba Linda, Calif.

[73] Assignee: Hemosphere Inc., Irvine, Calif.

[21] Appl. No.: 487,303

[22] Filed: Jun. 7, 1995

[51] Int. Cl.⁶ .................... A61K 9/16; A61K 47/42; B01J 8/00; B01J 13/00
[52] U.S. Cl. .................. 424/491; 424/490; 424/499; 427/2.14; 422/189
[58] Field of Search ................. 424/417, 499, 424/490, 491; 264/4.1, 4.3; 427/2.14, 213.33; 422/189

[56] References Cited

U.S. PATENT DOCUMENTS 5,069,936  12/1991  Yen ........................... 427/213.33
5,308,620   5/1994  Yen ................................ 424/484

Primary Examiner—Edward J. Webman

[57] ABSTRACT

A method and apparatus for large scale production of a product of in vivo medicine carriers which are medicine coated crosslinked protein microspheres for medicine administration. The reagents are prepared in solution and contained in respective bags. A series pumps and mixing chambers are connected to the reagent bags. The pumps are set at pre-determined rates and activated in a predetermined sequence within respective pre-determined delay periods, to achieve instantaneous component mixing and controlled sequential mixing characteristics.

47 Claims, 2 Drawing Sheets

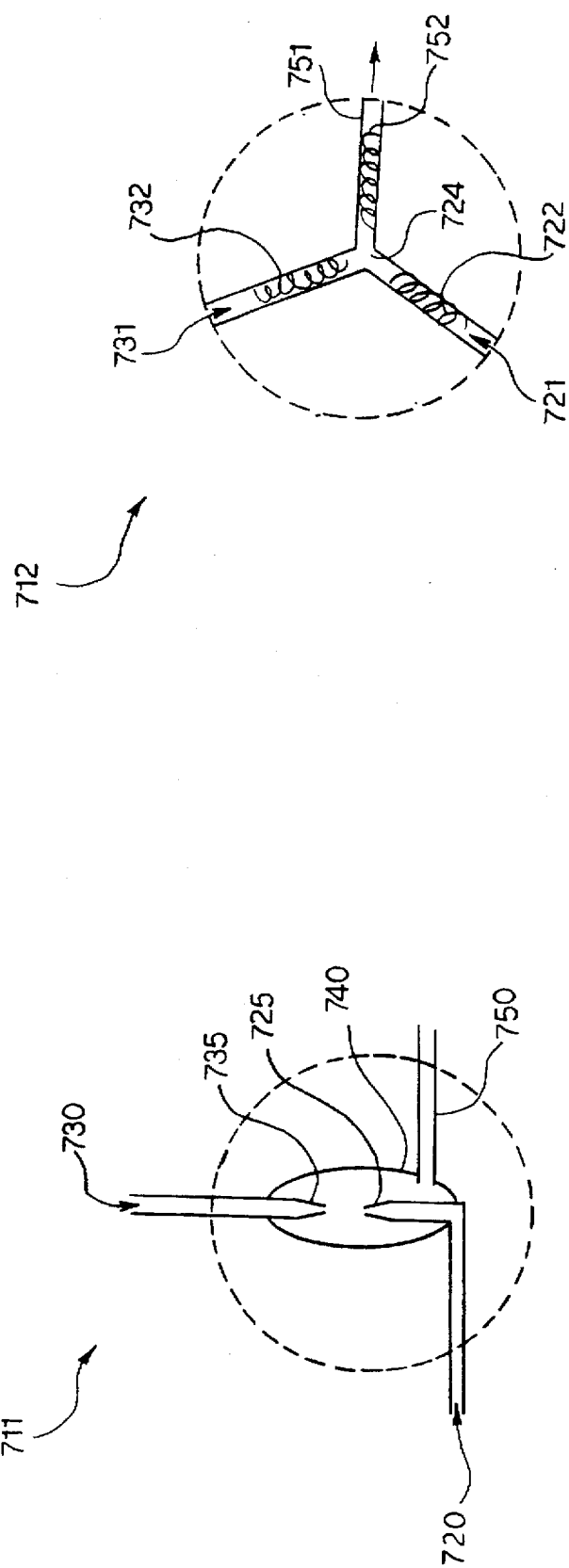

LARGE SCALE PRODUCTION OF MEDICINE COATED CROSSLINKED PROTEIN MICROSPHERES

BACKGROUND OF THE INVENTION

1. Field of the Invention

The present invention relates to the field of production of in vivo medicine carriers. More particularly the present invention relates to the field of large scale production of in vivo medicine carriers for intravenous or other routes (e.g., subcutaneous, intra-peritoneal, epidural or spinal) of drug administration.

2. Description of the Prior Art

Many manufacturing processes require the addition of components in a well defined sequence and controlled condition. Some critical steps may require instantaneous mixing of certain components to achieve uniformity of product properties.

For example, in the synthesis of spherical particles in a suspension medium, the instantaneous mixing of immiscible, semi-immiscible, or even completely miscible material before further stabilization will determine if the particles become homogeneous in size anal remain stable as monodispersed particles.

Another example will be the production of aerosol particles from more than two gaseous components, any two of which can react to form a solid particle. However, a well defined ratio of more than two components are desired within the final product, thereby requiring instantaneous contact of all the components within a small three dimensional space and within a very limited time allowance.

Such stringent requirements may be met if the reaction vessel is small in size so that all of the components can be introduced accurately in time and in the right amount and to achieve instantaneous mixing (e.g., in milli- or microseconds.) However, proportional enlargement of the same reaction vessel to achieve large scale production will not guarantee uniform mixing within the desired short time span.

The existing art mostly consists of vessels with a motorized blending blade to achieve quick mixing of components. Even so, the mixing may still not be quick enough. In addition, the large shearing force created by such mechanism may be destructive to the materials involved, or create unwanted air bubbles.

The entire process may also require sequential addition of multiple components. Variability in each step will compound the quality control problem. For example, suppose the first step requires the mixing of component A with component B to remit in the first intermediate component C. Assume further that due to poor mixing this step took two seconds to complete. Within these two seconds, some component A came into contact with component B within the first microsecond and started to grow in size, while other component A did not come into contact with component B until the last microsecond before the two seconds elapsed.

Therefore the result is to end up with a range of large and small C particles to start with after the two seconds. If one then wanted to add a color by mixing in component D and could not control the mixing condition then one would have a range of darker and lighter particles of small to largo sizes. But one could not get, for example, all small particles to be lighter color, and all large particles to be darker in color. It is obvious that the quality of the product becomes drastically more difficult to control as the number of steps are increased.

It is highly desirable to have a method which is suitable for large scale production to obtain uniform and controlled sequential mixing within a short time.

SUMMARY OF THE INVENTION

The present invention is method for a large scale production with instantaneous component mixing and controlled sequential mixing characteristics.

The present invention method is aimed at large scale production of products while achieving both uniform mixing within a short defined time and controlled sequential mixing. Uniform mixing is defined as achieving a proper ratio or amount of the components within a defined small space and achieved within an acceptable time span. Controlled sequential mixing means all the components are added in such a way that early finished intermediate product in step one will have the second component added early. Late finished intermediate product in step one will have the second component added late.

An analogy will be employees lining up in a single line in a company cafeteria to get food. Everyone picks up the bread first and then after a defined time, the vegetables, and then after a defined time, the meat, and then after another time span, the dessert. No cutting in line or mixing are allowed so that no one will get the meat first, or get everything but forget the vegetables. Such a process of controlled sequential mixing (or "first one in, first one out") will greatly enhance the uniformity of product characteristics.

Conceptually the present invention process may be explained as follows. If one can mix A and B instantaneously by shooting a quantity of A (e.g.,. 0.1 ml) by using a syringe and needle into a container containing 1 ml of component B, then one should be able to produce, e.g., 1 liter of the same product.

One could design a machine containing 1000 syringes and needles each containing 0.1 ml of A, injecting simultaneously into 1000 vessels each containing 1 ml or B. However, there is no compelling reason to inject all 1000 vessels at the same time. One could do it one vessel at a time, sequentially. One only needs to know which vessel reacted first so that addition of other components can follow the same sequence of vessels at the exact time intervals.

Applying this analogy, the present invention involves mixing of components in a small chamber, the design of which has been tested to allow complete mixing within the time span permitted. The components, whether in liquid, gas or solid form, are supplied continuously by a pump via tubings connected to the reservoirs containing the respective components. Therefore, the mixing chamber should have as many inlets as there are components and an outlet for the intermediate product.

Described generally, the present invention is a method for large scale production of a product of in vivo medicine carriers for intravenous drug administration. The present invention method includes the following basic steps.

The first main step is assembling a large scale production system. The large scale production system includes a protein unit including a protein bag and a protein pump connected downstream from the protein bag; a cross-linking unit including a cross-linking agent bag and a cross-linking agent pump connected downstream from the cross-linking agent bag; a medicine unit including a medicine bag and a medicine pump connected downstream from the medicine bag; a protein mixing chamber connected downstream from the protein and cross-linking agent pumps; a medicine mixing chamber connected downstream from the medicine pump and the protein mixing chamber; a delay means connected between the protein and medicine mixing chambers; a product collection bag connected to the medicine mixing chamber; and connection tubings interconnecting the bags, pumps, mixing chambers and collection bag.

The second main step is preparing a group of solutions of reagents including a protein, a cross-linking agent and a medicine. After the solutions are prepared, the substeps are filling the protein bag with a prepared solution of the protein; filling the crosslinking agent bag with a prepared solution of the cross-linking agent; and filling the medicine bag with a prepared solution of the medicine.

The third main step is setting respective pump rate of the pumps for mixing predetermined amounts of the reagents, and then activating the pumps in sequence for mixing the reagents in a pre-determined order within a pre-determined time period to produce the product. Particularly, the substeps includes: activating the protein pump to send the solution of the protein from the protein bag to the protein mixing chamber, and as soon as the solution of the protein from the protein bag reaches the protein mixing chamber, activating the cross-linking agent pump to send the solution of the cross-linking agent from the cross-linking agent bag to the protein mixing chamber, to thereby mix in the protein mixing chamber the solution of the protein from the protein bag with the solution of the cross-linking agent from the cross-linking agent bag, resulting in a solution containing cross-linked protein microspheres; and after a delay period determined by the delay means during which the solution of cross-linked protein microspheres reaches from the protein mixing chamber to the medicine mixing chamber, activating the medicine pump to send the solution of the medicine from the medicine bag to the medicine mixing chamber, to thereby mix in the medicine mixing chamber the solution of cross-linked protein microspheres from the protein mixing chamber with the solution of the medicine from the medicine bag, resulting in the product which is a solution of medicine-coated cross-linked protein microspheres.

The novel features of the present invention is that it achieves both uniform mixing within a short time period and controlled sequential mixing for large scale production.

Further novel features and other objects of the present invention will become apparent from the following detailed description, discussion and the appended claims, taken in conjunction with the drawings.

BRIEF DESCRIPTION OF THE DRAWINGS

Referring particularly to the drawings for the purpose of illustration only and not limitation, there is illustrated:

FIG. 2 is a preferred embodiment of a junction utilized in the present invention system shown in FIG. 1.

FIG. 3 is an alternative embodiment of a junction utilized in the present invention system shown in FIG. 1.

DESCRIPTION OF THE PREFERRED EMBODIMENT

Figure 1:
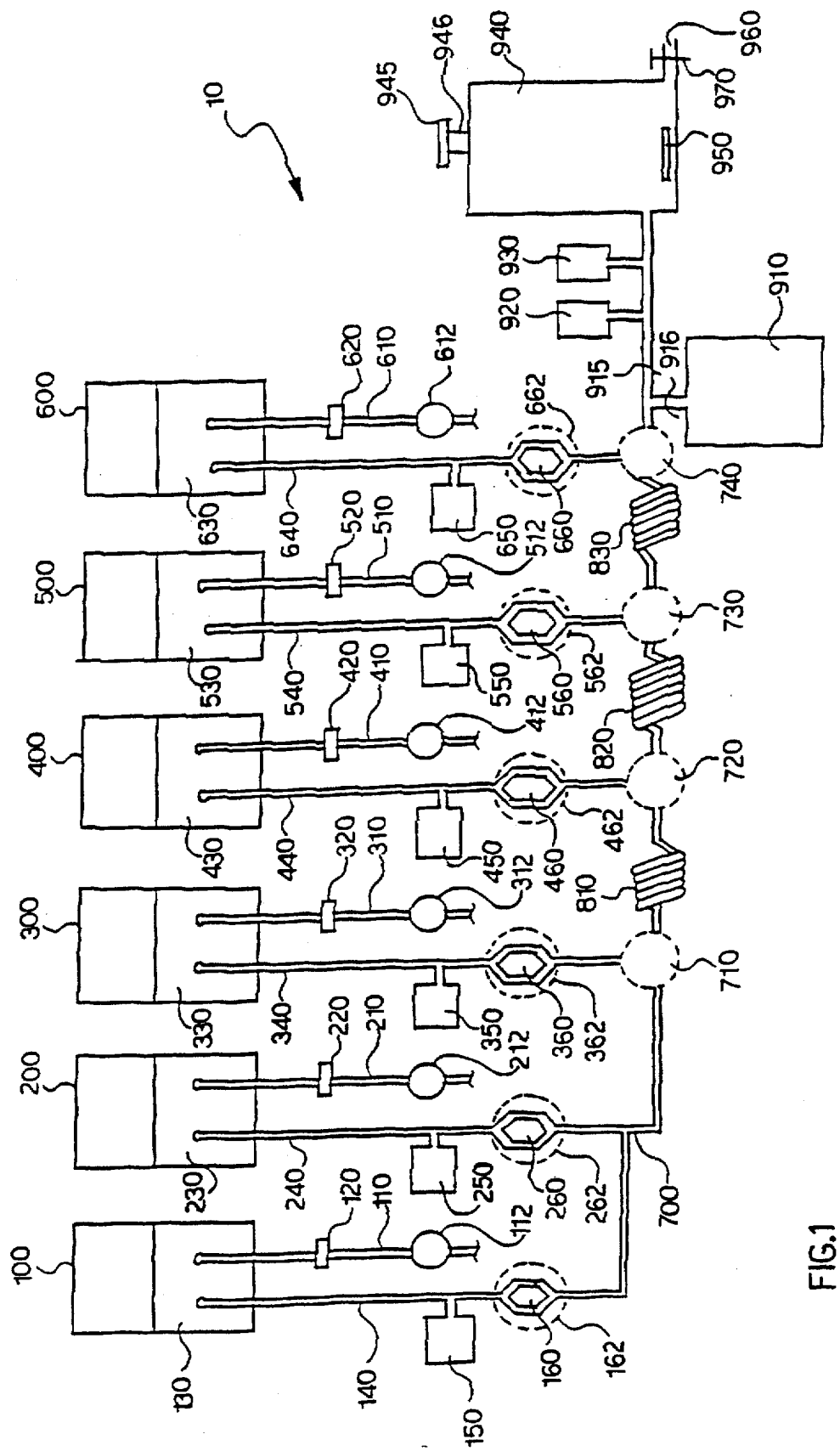
FIG. 1 is a schematic diagram of a system which utilizes the present invention method for a large scale production with instantaneous component mixing and controlled sequential mixing characteristics.

Although specific embodiments of the present invention will now be described with reference to the drawings, it should be understood that such embodiments are by way of example only and merely illustrative of but a small number of the many possible specific embodiments which can represent applications of the principles of the present invention. Various changes and modifications obvious to one skilled in the art to which the present invention pertains are deemed to be within the spirit, scope and contemplation of the present invention as further defined in the appended claims.

The present invention is described generally as follows. The present invention method is related to completely mixing of components in a small chamber within the time span permitted. The components, whether in liquid, gas or solid form, are continuously supplied by a pump via tubings connected to the reservoirs containing the respective components. The mixing chambers have respective inlets for infusion of the components, and an outlet for the intermediate product.

To allow addition of subsequent components, the first intermediate product will be pumped along a tubing, the length of which will cause a delay after which a third component can be added. For example, assume that component A is pumped in at 0.1 l/min and component B is pumped at a rate of 1 l/min into the first mixing chamber, and complete mixing is achieved within 1 microsecond. If it is desired that the third component D is to be added exactly after 3 minutes, then the tubings, e.g., with a internal cross-sectional area of 3 cm$^2$, should have a length of $$[(1\ l/min + 0.1\ l/min)/3\ cm^2] \times 3\ min = [(1.1 \times 1000\ cm^3/min)/3\ cm^2] \times 3\ min = 1,100\ cm$$

in between the outlet of the first mixing chamber and the inlet of the second mixing chamber.

The second chamber should have one inlet for the first intermediate product C, another inlet for component D, and an outlet for the second intermediate product E.

The system will not permit any vessels or containers (e.g., a beaker of at least 5.5 liter size to collect all the intermediates for 5 minutes) where intermediates are stored with the result that "early" intermediates are mixed with "late" intermediates before they are further pumped into other mixing chambers.

If all the components A, B, D, etc., are first filled in sterile bags or vessels, and bacterial filters are added to each tubing after the respective pumps for additional safety precaution (before the materials reached the mixing chambers), and the final bag to which the final product will flow has also been pre-sterilized, then the entire process is a closed system which will permit synthesis of sterile suspension products without the need of a sterile atmospheric environment (e.g., class 100 clean room.) This is particularly important since the suspension (which consists of protein particles typically 1 to 2 microns in diameter) cannot be subjected to 0.2 micron filtration to remove any potential bacterial contamination after the particles are formed, which will clog most filters.

Any mixing chamber that works can be connected to this system. However, a preferable design will be one where the inlet for component A will be 180 degrees opposite to the inlet for component B so that the two components will collide to achieve thorough mixing. The outlet for intermediate product C can be built anywhere in the mixing chamber but preferably at a site where unreacted component A or B are unlikely to exit without first having reacted or mixed with each other.

Another example of a mixing chamber will be a "static mixer" which can be fitted within the tubing itself immediately at the Y junction following the location where component A meets component B.

Referring to FIG. 1, there is shown at 10 a system which utilizes the present invention method for a large scale production with instantaneous component mixing and controlled sequential mixing characteristics.

As shown in FIG. 1, first reagent bag 100 comprises a reagent inlet 110, for infusion of reagent A (130) via a pump 112, through filter 120 into bag 100. Bag 100 also has an outlet 140 with a side sample bag 150 for sampling reagent A (130) for quality control. Double y-loop 160 will be fitted into a peristaltic pump 162 which will pump reagent A toward junction 700 and onward toward junction 710 and finally to "rinse fluid" collection bag 910 (with clamp 915 closed for this cycle).

The other reagent bags 200, 300, 400, 500 and 600 are similarly arranged for reagents B (230), C (330), D (430), E (530) and F (630) respectively. Therefore the description of these bags will not be repeated here. It is noted that the numerals denoting various parts of these bags are assigned in a manner corresponding to those used in denoting the first reagent bag 100.

As an example, the reagents of various bags may be as follows:

Reagent A (130): a suitable rinse fluid, e.g., normal saline;

Reagent B (230): 15% Human Serum Albumin (HSA) with Sodium Tetradecyl Sulfate (STS);

Reagent C (330): 70% ethanol;

Reagent D (430): 1.25% glutaraldehyde;

Reagent E (530): fibrinogen (1 mg/ml); and

Reagent F (630): dextrose 35%.

Junction 710 will take either format 711 (as shown in FIG. 2) or 712 (as shown in FIG. 3). Referring to FIG. 2, format 711 includes a mixing chamber 740 which has a first inlet 720 leading to chamber 740 with its inlet narrowing into a jet 725 to increase the velocity of the inlet stream if needed. Format 711 also has a second inlet 730 which permits infusion of a second ingredient (e.g., 70% ethanol). Inlet 730 likewise can narrow into another jet structure 735 to increase the rate of mixing.

The chamber 740 is not limited to two inlets. Multiple inlets will permit mixing of multiple ingredients. The different inlets can be situated at various angles relative to each other to facilitate the best mixing.

The chamber 740 should have little or no dead space where fluids are stagnant and not flushed out of the chamber 740 within a well defined time. The volume of the chamber 740 will be determined by the time it takes to achieve complete mixing. For example, if reagent A is pumped into the chamber 740 at a rate of 125 ml/min and reagent B is pumped into the chamber 740 at a rate of 225 ml/min, and it has been determined that the best mixing can be done in 0.1 minute, then the volume of the chamber 740 should be approximately:

$$(125 \text{ ml/min} + 225 \text{ ml/min}) \times 0.1 \text{ min} = 350 \text{ ml/min} \times 0.1 \text{ min} = 35 \text{ ml.}$$

The well mixed suspension/solution will exit the chamber via exit 750. Thereafter there will be a delay in the coil 810 (shown in FIG. 1) for completion of reaction or a fixed time of limited reaction.

Referring to FIG. 3, there is shown format 712 of junction 710. In situations where only two fluids need to be mixed and a special configuration of a chamber is not necessary for producing the desirable semi-finished product, static mixers can be placed inside the tubings to promote mixing of ingredients. Inlet 721 for infusion of reagent A has an optional static mixer 722 which can start turbulence so that when reagent A meets reagent B coming in via inlet 731 (which also has an optional static mixer 732) in the "dead space", the two reagents can start mixing even before they both pass through the main static mixer 752 which is placed inside the exit tubing 751. Obviously it is important to minimize the dead space 724 so that there is no imbalance of reagent A to reagent B within that space leading to uncontrolled and undesirable material formation.

Referring back to FIG. 1, the length of coils 810, 820, 830 will be determined by the desirable delay time, respectively, between reagents 230 and 330; and their product with reagent 430, and also the resulting product with reagent 530.

After the initial rinse cycle, the clamp 915 will be open and clamp 916 will be closed, to allow the final product to flow into collection container 940, which consists of a vent 946 with a sterile filter 945 and a magnetic or any other kind of stirrer 950. The container 940 also has an outlet 960 which has a clamp 970 on it.

Additional sample bags 920 and 930 may also be installed to permit samples of products to be collected and removed at any time (after double clamping) for quality control of the manufacturing process. The final product can be stored or dispensed soon under sterile conditions to various vials to be further processed.

The following are examples of detailed embodiments of the present invention. It is noted that these examples are given for the purpose of illustrating the present invention method, not as a limitation to its broad scope and various applications.

In one embodiment, the materials needed for the present invention process include:

(1) Stock Reagents needed to make the final product: e.g.
  (a) Human Serum Albumin (HSA) (25%);
  (b) a surfactant, e.g., sodium tetradecyl sulfate (STS) (3%);
  (c) ethanol (100%);
  (d) fibrinogen (dissolved as a 1 mg/ml solution in water); and
  (e) glutaraldehyde (25%);

(2) Material needed to assemble the "tube-set": all of which must be bio-compatible with the reagents and products and not shed material or become brittle with gamma radiation or gas or heat sterilization:
  (a) ⅛" to 1/16" internal diameter silicone tubings;
  (b) mixing chambers which may be used alone, or in conjunction with, or replaced by, polypropylene static mixers, which will be placed inside the silicone tubing near the mixing junctions;
  (c) polyethylene reagent bags (1, 5 or 10 liter) to hold reagent solutions;
  (d) sterile filters (to ensure sterility of reagents as they are pumped into the pre-sterilized polyethylene bags or protect the sterility of the vent in the product collection container); and
  (e) a collection container for the product which may contain a stirring mechanism to ensure "vial to vial" consistency when the product is dispensed into thousands of vials;

(3) Peristaltic pumps: to infuse diluents and stock reagents into reagent bags and to pump reagents from reagent bags into tubing at highly regulated rates to achieve effective mixing within a fixed time limit within the mixing chambers or via the static mixers at the mixing junctions; and (4) Temperature controls: heating or cooling blocks around the reagent bags or tubings or product container, if needed, to control the temperature of the reagents or the fluid inside the tubings or the mixing chambers.

In this embodiment, the steps of the present invention process include:

(1) Connect all tubings, bags, mixing chambers and collection container as depicted in FIG. 1;

(2) pack them in protective bags, gamma irradiation or gas or any appropriate method to sterilize;

(3) Open protective bag in clean-room; insert double-Y tubing into peristaltic pumps;

(4) Prepare solutions (if stock preparations need to be diluted, pre-add the correct diluent into bag before filling with stock preparations, all through the filter on the inlet to the bag) and making, e.g., fibrinogen cross-linking spheres:

(a) Reagent bag A: normal saline or water for flushing tubing before and after manufacturing;

(b) Reagent bag B: to get 3,433 ml of 15% HSA with correct concentration of STS in saline, first infuse into bag B 1,371 ml of saline, then add 2.39 ml of STS 3%; then infuse 2,060 ml of 25% stock HSA solution;

(c) Reagent bag C: contains a 70% alcohol solution (1,854 ml of water plus 4,327 ml of 100% ethanol);

(d) Reagent bag D contains a 1.25% glutaraldehyde solution: obtained by adding to 730 ml of saline approximately 38.4 ml of glutaraldehyde (stock solution at 25%); and (e) Reagent bag E contains a 1 mg/ml fibrinogen solution: 5280 ml of water plus 3.3 ml of STS plus 5.28 gm of fibrinogen (the STS is used to facilitate dissolution of fibrinogen);

(4) Set pump rates:

(a) Pump 162: 350±2 ml/min for pre-rinsing of tubing; stop after 5 liters of rinse is used up (the rinse fluid goes to a collection bag which will be discarded);

(b) Pump 262: 125±2 ml/min for pumping HSA;

(c) Pump 262: 225±0.5 ml/min (to start when HSA reaches junction 710) for pumping ethanol;

(d) Pump 462: 14±2 ml/min (to start when sphere suspension reaches junction 720) for pumping Glutaraldehyde;

(e) Pump 562: 182±0.5 ml/min (to start when sphere suspension reaches junction 730) for pumping fibrinogen; and (f) Pump 662: if an excipient (e.g., dextrose, for keeping the spheres apart and not sticking together during freeze-drying cycle) is needed or it is desirable to dilute (e.g., with water) the concentration of alcohol to minimize denaturing the protein spheres, pump 6 will be used to pump in this extra solution;

(5) Sequence of turning on pumps:

(a) turn on pump 162 for initial rinse cycle;

(b) after the initial rinse cycle (to remove any particulate matter inside the tubing set), stop pump 162, turn on pump 262;

(c) when the HSA reaches the mixing junction 710, turn on pump 362;

(d) when the turbid suspension reaches junction 720, turn on pump 462;

(e) when the partially stabilized spheres reach junction 730, turn on pump 562; and (f) when the fibrinogen coated spheres reach junction 740, turn on pump 662.

(6) When the desired volume of product is achieved, stop pump 362 first (because excess alcohol added to HSA will form aggregates), then stop pump 262 and then at the corresponding delay time, stop pump 462, 562 and 662 (the delay time is defined as the time it takes partially processed material to move from one mixing junction to the next mixing junction; the delay or lag time is needed for completion or partial completion of reaction of all previously mixed material before the next ingredient is added); and (7) Start pump 162 again at the time pump 362 is shut off, to push out products inside the tubings toward product collection container 940 (because of the substantial length of delay segments, the amount of material inside the tubings can be substantial and costly).

The results of the above sample production process is described as follows. When the product collected in the product collection container 940 is analyzed, the number of spheres/ml typically ranges from approximately 2 to 9 billion particles/ml as measured by the Coulter counter (which only can measure particle sizes greater than 0.6 microns in diameter) and the mean diameter is approximately 1.1 micron. By controlling the various pump rates of the various pumps, particle size with a range of 0.8 to 1.6 microns can easily be made. Scanning Electron Microscopy (SEM) techniques show that when the mean of the spheres are about 1.1 microns, about 30 to 50% of the particles are actually less than 0.6 microns. Therefore, potentially up to 18 billion particles of all sizes can be produced per ml of suspension.

After the suspension is filled into vials, the contents will be quickly frozen and subjected to lyophilization under sterile conditions. The mean size of the spheres did not substantially change with lyophilization followed by reconstitution with normal saline. The majority of glutaraldehyde molecules are expected to have completely reacted during storage before freeze-drying with the residual proteins in the supernatant or with the protein spheres. The amount of "reactive" glutaraldehyde left after reconstitution of the powdery lyophilized protein spheres with normal saline typically is below 0.03%. Ethanol is removed almost completely by the lyophilization process, with less than 0.5% left in the supernatant of the reconstituted suspension. In addition, the pH value of the suspension is typically 6.0 to 7.5.

It is noted that the medicine added into the product may be mixed in different steps. For example, the solution containing medicine may be mixed with the protein solution before or after adding the alcohol, and before or after adding a stabilizer.

In the present invention, the stabilizing agents or stabilizers used may be selected from a group consisting of Glutaraldehyde, Glutathione, Sodium Sulfite, Sodium Bisulfite, Nicotinamide Adenine Dinucleotide Phosphate (NADP), Dithiothreitol (DTT), Polyethylene Glycol (PEG), 2-Mercaptoethanol, 1-Ketoglutaric Acid, Gamma-aminolevulinic Acid, N-acetylneuraminic Acid, DL Lactic Acid, Thioctic Acid, Succinic Acid, Ascorbic Acid, Stannous Chloride, Manganese Chloride, Magnesium Chloride, Gentamycin, Poly-L-lysine, Cysteine and Dimethyl Sulfoxide.

Table One on the next page lists chemical compounds which are useful in stabilizing protein particles against subsequent resolubilization. Effective concentrations of agents after being mixed with sphere suspensions in the presence of alcohol. Therefore, if the ratio of the flow rate of other material entering junction 720 (e.g., 1000 ml/min) and the pump rate of pump 462 (e.g. 10 ml/min) is Y (e.g., 100), then the concentration of the agent in bag 400 will be increased by Y fold compared to the effective concentration listed in Table One. Minimal effective concentrations are those below which spheres will resolubilize in subsequent steps where the alcohol concentration will be reduced by non-alcohol containing fluids. Maximal effective concentrations are those above which spheres will tend to aggregate to result in large uncontrollable agglomerates. Effective concentrations may vary depending on the incubation time with protein particles or the concentrations of proteins.

In Table One:
* incubation time between agent and sphere suspension was 2 hours, all other incubation times were approximately 18 hours;
** lowest final concentration tested was 10 micromolar;
*** highest final concentration tested was 2,500 micromolar; and

**** initial concentration of HSA was 5%, instead of 15% which required approximately double the minimum concentration of agent to achieve stability against resolubilization.

TABLE ONE

| | Effective Concentrations (micromolar) | |
|---|---|---|
| Agent | Minimum | Maximum |
| Sodium Bisulfite* | 650 | 5,000 |
| Sodium Sulfite | 500 | 2,500 |
| NADP* | 250 | 2,500 |
| DTT* | 100 | 1,000 |
| Glutathione* | 100 | 2,500*** |
| PEG (MW 2,600)* | 12.5 | 2,500 μg/ml |
| PEG(MW 5,000)* | 12.5 | 2,500 μg/ml |
| PEG (MW 8,000)* | 12.5 | 2,500 μg/ml |
| Sodium Bisulfite | 50 | 500 |
| Sodium Sulfite | 50 | 500 |
| 2-Mercaptoethanol | 10** | 5,000 |
| DL Lactic Acid | 500 | 1,000 |
| Thioctic Acid | 10 | 500 |
| Stannous Chloride | 250 | 2,500 |
| Succinic Acid**** | 1,000 | 2,500 |
| Ascorbic Acid**** | 1,000 | 2,500 |
| 1-Ketoglutaric Acid**** | 1,000 | 1,000 |
| Cysteine**** | 500 | 2,500 |
| Manganese Chloride**** | 1,000 | 2,500 |
| Magnesium Chloride | 5,000 | Not |
| Gamma-Aminolevulinic Acid | 2 | evaluated. |
| Gentamycin | 0.05 mg/ml | |
| Poly-L-lysine (MW 147,000 and 430,500) | 0.1 mg/ml | |
| N-acetylneuraminic Acid | 0.5 mg/ml | |
| Dimethyl Sulfoxide | 1/100 dilution | |

The major advantage of the present invention is that it is suitable for large scale production of in vivo medicine carriers for intravenous drug administration and achieves both uniform mixing within a short time period and controlled sequential mixing.

Defined in detail, the present invention is a method for large scale production of a product of in vivo medicine carriers for intravenous drug administration. The method comprises the following basic steps.

First, a large scale production system is assembled. The system includes: (i) a first reagent unit including a first reagent bag and a first pump connected downstream from the first reagent bag; (ii) a second reagent unit including a second reagent bag and a second pump connected downstream from the second reagent bag; (iii) a third reagent unit including a third reagent bag and a third pump connected downstream from the third reagent bag; (iv) a fourth reagent unit including a fourth reagent bag and a fourth pump connected downstream from the fourth reagent bag; (v) a fifth reagent unit including a fifth reagent bag and a fifth pump connected downstream from the fifth reagent bag; (vi) a sixth reagent unit including a sixth reagent bag and a sixth pump connected downstream from the sixth reagent bag; (vii) a first mixing chamber connected downstream from the first, second and third pumps; (viii) a second mixing chamber connected downstream from the fourth pump and the first mixing chamber; (ix) a third mixing chamber connected downstream from the fifth pump and the second mixing chamber; (x) a fourth mixing chamber connected downstream from the sixth pump and the third mixing chamber; (xi) a first delay coil connected between the first and second mixing chambers; (xii) a second delay coil connected between the second and third mixing chambers; (xiii) a third delay coil connected between the third and fourth mixing chambers; (xiv) a rinse fluid collection bag connected to the fourth mixing chamber via a first valve means; (xv) a product collection bag also connected to the fourth mixing chamber via a second valve means; and (xvi) connection tubings interconnecting the reagent bags, pumps, mixing chambers, valves and collection bags.

Second, the large scale production system is sterilized. Then a group of solutions of reagents is prepared. The reagents include proteins, surfactants, alcohols, stabilizing agents, medicines and post-treatment agents. The bags are then filled with the prepared solutions respectively. This is done by (i) filling the first reagent bag with the normal saline; (ii) filling the second reagent bag with a prepared solution of the albumin and the surfactant; (iii) filling the third reagent bag with a prepared solution of the alcohol; (iv) filling the fourth reagent bag with a prepared solution of the stabilizing agent; (v) filling the fifth reagent bag with a prepared solution of the medicine and the surfactant; and (vi) filling the sixth reagent bag with a prepared solution of the post-treatment agent.

Third, the respective pump rate of the pumps are set for mixing pre-determined mounts of the reagents. The first pump is activated first to rinse the mixing chambers, delay coils and connection tubings with the normal saline from the first reagent bag, and the first valve means is opened to collect the normal saline in the rinse fluid collection bag. Afterwards the first pump is deactivated, the first valve means is closed, and the second valve means is opened, so that the production collection bag is ready for collecting the product.

The fourth step is most important, during which the pumps are activated in sequence for mixing the reagents in a pre-determined order within a pre-determined time period to produce the product. This step includes the following sub-steps: (i) activating the second pump to send the solution of the albumin and surfactant from the second reagent bag to the first mixing chamber, and as soon as the solution of the albumin and surfactant from the second reagent bag reaches the first mixing chamber, activating the third pump to send the solution of the alcohol from the third reagent bag to the first mixing chamber, to thereby mix in the first mixing chamber the solutions of the albumin and surfactant from the second reagent bag with the solution of the alcohol from the third reagent bag, resulting in a solution containing turbid suspension of monodispersed albumin microspheres; (ii) after a first delay period determined by the first delay coil during which the solution of turbid suspension reaches from the first mixing chamber to the second mixing chamber, activating the fourth pump to send the solution of the stabilizer from the fourth reagent bag to the second mixing chamber, to thereby mix in the second mixing chamber the solution of turbid suspension from the first mixing chamber with the solution of the stabilizer from the fourth reagent bag, resulting in a solution of partially stabilized albumin microspheres; (iii) after a second delay period determined by the second delay coil during which the solution of partially stabilized microspheres reaches from the second mixing chamber to the third mixing chamber, activating the fifth pump to send the solution of the medicine from the fifth reagent bag to the third mixing chamber, to thereby mix in the third mixing chamber the solution of partially stabilized microspheres from the second mixing chamber with the solution of the medicine from the fifth reagent bag, resulting in a solution of partially stabilized, monodispersed and medicine-coated albumin microspheres; and (iv) after a third delay period determined by the third delay coil during which the solution of medicine-coated microspheres reaches from the third mixing chamber to the fourth mixing chamber, activating the sixth pump to send the solution of the post-treatment agent from the sixth reagent bag to the fourth mixing chamber, to thereby mix in the fourth mixing chamber the solution of medicine coated microspheres from the third mixing chamber with the solution of the post-treatment agent from the sixth reagent bag, resulting in the product which is a solution of stabilized, monodispersed and medicine coated albumin microspheres.

The product is collected in the product collection bag. After a desired amount of the product is collected, the second valve means is closed, and the pumps are deactivated in sequence to prevent aggregation in the product. This is done as follows: (i) first deactivating the third pump to stop sending the alcohol from the third reagent bag into the first mixing chamber; (ii) after the first delay time, deactivating the fourth pump to stop sending the stabilizer from the fourth reagent bag into the second mixing chamber; (iii) after the second delay time, deactivating the fifth pump to stop sending the medicine from the fifth reagent bag into the third mixing chamber; and (iv) after the third delay time, deactivating the sixth pump to stop sending the post-treatment agent from the sixth reagent bag into the fourth mixing chamber.

It is important that at about the same time the third pump is deactivated, the first pump is activated again to rinse the mixing chambers, delay coils and connection tubings again with the normal saline from the first reagent bag, to flush the residual products in the tubings with the normal saline into the product collection bag.

Defined alternatively, the present invention is also an apparatus for large scale production of a product of in vivo medicine carriers for intravenous drug administration. The present invention apparatus comprises a large scale production system which essentially includes: (i) a protein unit including a protein bag and a protein pump connected downstream from the protein bag; (ii) a cross-linking unit including a cross-linking agent bag and a cross-linking agent pump connected downstream from the crosslinking agent bag; and (iii) a medicine unit including a medicine bag and a medicine pump connected downstream from the medicine bag; (iv) a protein mixing chamber connected downstream from the protein and cross-linking agent pumps; (v) a medicine mixing chamber connected downstream from the medicine pump and the protein mixing chamber; (vi) a delay means connected between the protein and medicine mixing chambers; (vii) a product collection bag connected to the medicine mixing chamber for collecting the product; and (viii) connection tubings interconnecting the bags, pumps, mixing chambers and collection bag.

The bags are respectively filled with a group of solutions of reagents including a protein, a cross-linking agent and a medicine, where (i) the protein bag is filled with a prepared solution of the protein; (ii) the cross-linking agent bag is filled with a prepared solution of the cross-linking agent; and (iii) the medicine bag is filled with a prepared solution of the medicine.

The pumps are set at respective pump rates for mixing pre-determined amounts of the reagents. The pumps are activated in sequence for mixing the reagents in a predetermined order within a pre-determined time period to produce the product, where (i) the protein pump is activated to send the solution of the protein from the protein bag to the protein mixing chamber, and as soon as the solution of the protein from the protein bag reaches the protein mixing chamber, the cross-linking agent pump is activated to send the solution of the cross-linking agent from the cross-linking agent bag to the protein mixing chamber, to thereby mix in the protein mixing chamber the solution of the protein from the protein bag with the solution of the cross-linking agent from the cross-linking agent bag, resulting in a solution containing cross-linked protein microspheres; and (ii) after a delay period determined by the delay means during which the solution of cross-linked protein microspheres reaches from the protein mixing chamber to the medicine mixing chamber, the medicine pump is activated to send the solution of the medicine from the medicine bag to the medicine mixing chamber, to thereby mix in the medicine mixing chamber the solution of cross-linked protein microspheres from the protein mixing chamber with the solution of the medicine from the medicine bag, resulting in the product which is a solution of medicine-coated cross-linked protein microspheres.

Of course the present invention is not intended to be restricted to any particular form or arrangement, or any specific embodiment disclosed herein, or any specific use, since the same may be modified in various particulars or relations without departing from the spirit or scope of the claimed invention hereinabove shown and described of which the apparatus shown is intended only for illustration and for disclosure of an operative embodiment and not to show all of the various forms or modification in which the present invention might be embodied or operated.

The present invention has been described in considerable detail in order to comply with the patent laws by providing full public disclosure of at least one of its forms. However, such detailed description is not intended in any way to limit the broad features or principles of the present invention, or the scope of patent monopoly to be granted.

What is claimed is:

1. A method for large scale production of a product of in vivo medicine carriers for medicine administration, comprising the steps of:

a. assembling a large scale production system including:

i) a first reagent unit including a first reagent bag and a first pump connected downstream from said first reagent bag;

ii) a second reagent unit including a second reagent bag and a second pump connected downstream from said second reagent bag;

iii) a third reagent unit including a third reagent bag and a third pump connected downstream from said third reagent bag;

iv) a fourth reagent unit including a fourth reagent bag and a fourth pump connected downstream from said fourth reagent bag;

v) a fifth reagent unit including a fifth reagent bag and a fifth pump connected downstream from said fifth reagent bag;

vi) a sixth reagent unit including a sixth reagent bag and a sixth pump connected downstream from said sixth reagent bag;

vii) a first mixing chamber connected downstream from said first, second and third pumps;

viii) a second mixing chamber connected downstream from said fourth pump and said first mixing chamber;

ix) a third mixing chamber connected downstream from said fifth pump and said second mixing chamber;

x) a fourth mixing chamber connected downstream from said sixth pump and said third mixing chamber;

xi) a first delay coil connected between said first and second mixing chambers;

xii) a second delay coil connected between said second and third mixing chambers;

xiii) a third delay coil connected between said third and fourth mixing chambers;

xiv) a rinse fluid collection bag connected to said fourth mixing chamber via a first valve means;

xv) a product collection bag also connected to said fourth mixing chamber via a second valve means; and xvi) connection robings interconnecting said reagent bags, pumps, mixing chambers, valves and collection bags;

b. sterilizing said large scale production system;

c. preparing a suitable rinse solution and respective solutions of a group of reagents including an albumin, a surfactant, an alcohol, a cross-linking agent, a medicine and a post-treatment agent, and i) filling said first reagent bag with said rinse solution;

ii) filling said second reagent bag with a prepared solution of said albumin and said surfactant;

iii) filling said third reagent bag with a prepared solution of said alcohol;

iv) filling said fourth reagent bag with a prepared solution of said cross-linking agent;

v) filling said fifth reagent bag with a prepared solution of said medicine; and vi) filling said sixth reagent bag with a prepared solution of said post-treatment agent;

d. setting respective pump rates of said pumps for mixing pre-determined amounts of said reagents;

e. activating said first pump to rinse said mixing chambers, delay coils and connection tubings with said rinse solution from said first reagent bag, and opening said first valve means to collect said rinse solution in said rinse fluid collection bag;

f. deactivating said first pump, closing said first valve means and opening said second valve means such that said production collection bag is ready for collecting said product;

g. activating said pumps in sequence for mixing said reagents in a predetermined order within a pre-determined time period to produce said product, including:

i) activating said second pump to send said solution of said albumin and surfactant from said second reagent bag to said first mixing chamber, and as soon as said solution of said albumin and surfactant from said second reagent bag reaches said first mixing chamber, activating said third pump to send said solution of said alcohol from said third reagent bag to said first mixing chamber, to thereby mix in said first mixing chamber said solutions of said albumin and surfactant from said second reagent bag with said solution of said alcohol from said third reagent bag, resulting in a solution containing turbid suspension of monodispersed albumin microspheres;

ii) after a first delay period determined by said first delay coil during which said solution of turbid suspension reaches from said first mixing chamber to said second mixing chamber, activating said fourth pump to send said solution of said cross-linking agent from said fourth reagent bag to said second mixing chamber, to thereby mix in said second mixing chamber said solution of turbid suspension from said first mixing chamber with said solution of said cross-linking agent from said fourth reagent bag, resulting in a solution of partially cross-linked albumin microspheres;

iii) after a second delay period determined by said second delay coil during which said solution of partially cross-linked microspheres reaches from said second mixing chamber to said third mixing chamber, activating said fifth pump to send said solution of said medicine from said fifth reagent bag to said third mixing chamber, to thereby mix in said third mixing chamber said solution of partially cross-linked microspheres from said second mixing chamber with said solution of said medicine from said fifth reagent bag, resulting in a solution of partially cross-linked, monodispersed and medicine-coated albumin microspheres; and iv) after a third delay period determined by said third delay coil during which said solution of medicine-coated microspheres reaches from said third mixing chamber to said fourth mixing chamber, activating said sixth pump to send said solution of said post-treatment agent from said sixth reagent bag to said fourth mixing chamber, to thereby mix in said fourth mixing chamber said solution of medicine coated microspheres from said third mixing chamber with said solution of said post-treatment agent from said sixth reagent bag, resulting in said product which is a solution of cross-linked, monodispersed and medicine coated albumin microspheres;

h. collecting said product in said product collection bag;

i. after a desired amount of said product is collected, closing said second valve means, and deactivating said pumps in sequence to prevent aggregation in said product, including:

i) first deactivating said third pump to stop sending said alcohol from said third reagent bag into said first mixing chamber;

ii) after said first delay time, deactivating said fourth pump to stop sending said cross-linking agent from said fourth reagent bag into said second mixing chamber;

iii) after said second delay time, deactivating said fifth pump to stop sending said medicine from said fifth reagent bag into said third mixing chamber; and iv) after said third delay time, deactivating said sixth pump to stop sending said post-treatment agent from said sixth reagent bag into said fourth mixing chamber; and j. as soon as said third pump is deactivated, activating said first pump to rinse said mixing chambers, delay coils and connection tubings again with said rinse solution from said first reagent bag, rinsing residuals of said product from said mixing chambers, delay coils and connection tubings into said product collection bag;

k. whereby said large scale production method produces said product of cross-linked, monodispersed and medicine coated albumin microspheres which are useful as in vivo medicine carriers for medicine administration.

2. The method as defined in claim 1 wherein said step of preparing said solutions further includes the step of dilution.

3. The method as defined in claim 1 wherein said step of preparing said solutions further includes the step of filtration.

4. The method as defined in claim 1 wherein said rinse solution is normal saline.

5. The method as defined in claim 1 wherein said albumin is human serum albumin.

6. The method as defined in claim 1 wherein said surfactant is sodium tetradecyl sulfate.

7. The method as defined in claim 1 wherein said alcohol is ethanol.

8. The method as defined in claim 1 wherein said cross-linking agent is selected from a group consisting of glutaraldehyde, glutathione, sodium sulfite, sodium bisulfite, nicotinamide adenine dinucleotide phosphate, dithiothreitol, polyethylene glycol, 2-mercaptoethanol, 1-ketoglutaric acid, gamma-aminolevulinic acid, N-acetylneuraminic acid, DL lactic acid, thioctic acid, succinic acid, ascorbic acid, stannous chloride, manganese chloride, magnesium chloride, gentamycin, poly-l-lysine, cysteine and dimethyl sulfoxide.

9. The method as defined in claim 1 wherein said medicine is fibrinogen.

10. The method as defined in claim 1 wherein said post-treatment agent is dextrose.

11. A device produced by the method as defined in claim 1.

12. A method for large scale production of a product of in vivo medicine carriers, comprising the steps of:
   a. assembling a large scale production system including:
      i) a protein unit including a protein bag and a protein pump connected downstream from said protein bag;
      ii) an alcohol unit including an alcohol bag and an alcohol pump connected downstream from said alcohol bag;
      iii) a cross-linking agent unit including a cross-linking agent bag and a cross-linking agent pump connected downstream from said cross-linking agent bag;
      iv) a medicine unit including a medicine bag and a medicine pump connected downstream from said medicine bag;
      v) a first mixing chamber connected downstream from said protein and alcohol pumps;
      vi) a second mixing chamber connected downstream from said cross-linking agent pump and said first mixing chamber;
      vii) a third mixing chamber connected downstream from said medicine pump and said second mixing chamber;
      viii) a first delay means connected between said first and second mixing chambers;
      ix) a second delay means connected between said second and third mixing chambers;
      x) a product collection bag connected to said third mixing chamber; and
      xi) connection tubings interconnecting said bags, pumps, mixing chambers and collection bag;
   b. preparing respective solutions of a group of reagents including a protein, an alcohol, a cross-linking agent and a medicine, and
      i) filling said protein bag with a prepared solution of said protein;
      ii) filling said alcohol agent bag with a prepared solution of said alcohol;
      iii) filling said cross-linking agent bag with a prepared solution of said cross-linking agent; and
      iv) filling said medicine bag with a prepared solution of said medicine;
   c. setting respective pump rates of said pumps for mixing pre-determined amounts of said reagents;
   d. activating said pumps in sequence for mixing said reagents in a predetermined order within a pre-determined time period to produce said product, including:
      i) activating said protein pump to send said solution of said protein from said protein bag to said first mixing chamber, then activating said alcohol pump to send said solution of said alcohol from said alcohol bag to said first mixing chamber, to thereby mix therein said solution of said protein with said solution of said alcohol, resulting in a solution containing protein microspheres;
      ii) after a first delay period determined by said first delay means, activating said cross-linking agent pump to send said solution of said cross-linking agent from said cross-linking agent bag to said second mixing chamber, to thereby mix therein said solution of protein microspheres with said solution of said cross-linking agent, resulting in a solution of cross-linked protein microspheres; and
      iii) after a second delay period determined by said delay means, activating said medicine pump to send said solution of said medicine from said medicine bag to said third mixing chamber, to thereby mix therein said solution of cross-linked protein microspheres with said solution of said medicine, resulting in said product which is a solution of medicine-coated cross-linked protein microspheres; and
   e. collecting said product in said product collection bag;
   f. whereby said large scale production method produces said product of medicine coated cross-linked protein microspheres which are useful as in vivo medicine carriers for medicine administration.

13. The method as defined in claim 12 further including the step of sterilizing said large scale production system before using it to produce said product.

14. The method as defined in claim 12 further including the step of rinsing said large scale production system before using it to produce said product.

15. The method as defined in claim 12 further including the step of mixing a solution of post-treatment agent to said solution of medicine-coated cross-linked protein microspheres for post-production stabilization.

16. The method as defined in claim 12 further including the step of rinsing said large scale production system after using it to produce said product.

17. The method as defined in claim 12 wherein said protein is selected from a group including albumin and hemoglobin.

18. The method as defined in claim 12 wherein said alcohol is ethanol.

19. The method as defined in claim 12 wherein said cross-linking agent is selected from a group consisting of glutaraldehyde, glutathione, sodium sulfite, sodium bisulfite, nicotinamide adenine dinucleotide phosphate, dithiothreitol, polyethylene glycol, 2-mercaptoethanol, 1-ketoglutaric acid, gamma-aminolevulinic acid, N-acetylneuraminic acid, DL lactic acid, thioctic acid, succinic acid, ascorbic acid, stannous chloride, manganese chloride, magnesium chloride, gentamycin, poly-l-lysine, cysteine and dimethyl sulfoxide.

20. The method as defined in claim 12 wherein said medicine is fibrinogen.

21. The method as defined in claim 15 wherein said post-treatment agent is dextrose.

22. A device produced by the method as defined in claim 12.

23. A method for large scale production of a product of in vivo carriers, comprising the steps of:
   a. assembling a large scale production system including:
      i) a protein unit including a protein bag and a protein pump connected downstream from said protein bag;
      ii) an alcohol unit including an alcohol bag and an alcohol pump connected downstream from said alcohol bag;
      iii) a cross-linking agent unit including a cross-linking agent bag and a cross-linking agent pump connected downstream from said cross-linking agent bag;
      iv) a first mixing chamber connected downstream from said protein and alcohol pumps;
      v) a second mixing chamber connected downstream from said cross-linking agent pump and said first mixing chamber;
      vi) a product collection bag connected to said third mixing chamber; and
      vii) connection tubings interconnecting said bags, pumps, mixing chambers and collection bag;
   b. preparing respective solutions of a group of reagents including a protein, an alcohol and a cross-linking agent, and
      i) filling said protein bag with a prepared solution of said protein;
      ii) filling said alcohol agent bag with a prepared solution of said alcohol; and
      iii) filling said cross-linking agent bag with a prepared solution of said cross-linking agent;
   c. setting respective pump rates of said pumps for mixing pre-determined amounts of said reagents;
   d. activating said pumps in sequence for mixing said reagents in a predetermined order within a pre-determined time period to produce said product, including:
      i) activating said protein pump to send said solution of said protein from said protein bag to said first mixing chamber, then activating said alcohol pump to send said solution of said alcohol from said alcohol bag to said first mixing chamber, to thereby mix therein said solution of said protein with said solution of said alcohol, resulting in a solution containing protein spheres; and
      ii) activating said cross-linking agent pump to send said solution of said cross-linking agent from said cross-linking agent bag to said second mixing chamber, to thereby mix therein said solution of protein spheres with said solution of said cross-linking agent, resulting in a solution of cross-linked protein spheres; and
   e. collecting said product in said product collection bag;
   f. whereby said large scale production method produces said product of cross-linked protein spheres which are useful as in vivo carriers.

24. The method as defined in claim 23 further including the step of sterilizing said large scale production system before using it to produce said product.

25. The method as defined in claim 23 further including the step of rinsing said large scale production system before using it to produce said product.

26. The method as defined in claim 23 further including the step of mixing a solution of medicine for producing a solution of cross-linked protein spheres carrying medicine.

27. The method as defined in claim 26 wherein said solution of medicine is mixed with said solution of protein.

28. The method as defined in claim 26 wherein said solution of medicine is mixed with said solution of protein spheres.

29. The method as defined in claim 26 wherein said solution of medicine is mixed with said solution of cross-linked protein spheres.

30. The method as defined in claim 23 further including the step of mixing a solution of post-treatment agent to said solution of cross-linked protein spheres for post-production stabilization.

31. The method as defined in claim 23 further including the step of rinsing said large scale production system after using it to produce said product.

32. The method as defined in claim 23 wherein said protein is selected from a group including albumin and hemoglobin.

33. The method as defined in 23 wherein said alcohol is ethanol.

34. The method as defined in claim 23 wherein said cross-linking agent is selected from a group consisting of glutaraldehyde, glutathione, sodium sulfite, sodium bisulfite, nicotinamide adenine dinucleotide phosphate, dithiothreitol, polyethylene glycol, 2-mercaptoethanol, 1-ketoglutaric acid, gamma-aminolevulinic acid, N-acetylneuraminic acid, DL lactic acid, thioctic acid, succinic acid, ascorbic acid, stannous chloride, manganese chloride, magnesium chloride, gentamycin, poly-1-lysine, cysteine and dimethyl sulfoxide.

35. The method as defined in claim 26 wherein said medicine is fibrinogen.

36. The method as defined in claim 30 wherein said post-treatment agent is dextrose.

37. A device produced by the method as defined in claim 23.

38. An apparatus for large scale production of a product of in vivo medicine carriers for medicine administration, comprising:
   a. a large scale production system including:
      i) a protein unit including a protein bag and a protein pump connected downstream from said protein bag;
      ii) an alcohol unit including an alcohol bag and an alcohol pump connected downstream from said alcohol bag; and
      iii) a cross-linking agent unit including a cross-linking agent bag and a cross-linking agent pump connected downstream from said cross-linking agent bag;
      iv) a first mixing chamber connected downstream from said protein and alcohol pumps;
      v) a second mixing chamber connected downstream from said cross-linking agent pump and said first mixing chamber;
      vi) a product collection bag connected to said medicine mixing chamber for collecting said product; and
      vii) connection tubings interconnecting said bags, pumps, mixing chambers and collection bag;
   b. said bags filled with respective solutions of a group of reagents including a protein, an alcohol, and a cross-linking agent, where
      i) said protein bag is filled with a prepared solution of said protein;
      ii) said alcohol bag is filled with a prepared solution of said alcohol; and
      iii) said cross-linking agent bag is filled with a prepared solution of said cross-linking agent;
   c. said pumps set at respective pump rates for mixing pre-determined amounts of said reagents;
   d. said pumps activated in sequence for mixing said reagents in a predetemined order within a pre-determined time period to produce said product, where i) said protein pump is activated to send said solution of said protein from said protein bag to said first mixing chamber, then said alcohol pump is activated to send said solution of said alcohol from said alcohol bag to said first mixing chamber, to thereby mix therein said solution of said protein with said solution of said alcohol, resulting in a solution containing protein spheres; and ii) said cross-linking agent pump is activated to send said solution of said cross-linking agent from said cross-linking agent bag to said second mixing chamber, to thereby mix therein said solution of protein spheres with said solution of said cross-linking agent, resulting in said product which is a solution of cross-linked protein spheres;

e. whereby said large seal production apparatus produces said product of medicine coated cross-linked protein microspheres which are useful as in vivo medicine carriers for medicine administration.

39. The apparatus as defined in claim 38 wherein said mixing chambers each has two inlet nozzles arranged 180 degrees opposite to each other to enhance the mixing.

40. The apparatus as defined in claim 38 wherein said mixing chambers are static mixers.

41. The method as defined in claim 38 further comprising means for sterilizing said large scale production system before using it to produce said product.

42. The method as defined in claim 38 further comprising means for rinsing said large scale production system before using it to produce said product.

43. The apparatus as defined in claim 38 further comprising means for mixing a solution of medicine to said solution of said protein for producing a solution of stabilized protein spheres carrying medicine.

44. The apparatus as defined in claim 38 further comprising means for mixing a solution of medicine to said solution of protein spheres for producing a solution of stabilized protein spheres carrying medicine.

45. The apparatus as defined in claim 38 further comprising means for mixing a solution of medicine to said solution of stabilized protein spheres for producing a solution of stabilized protein spheres carrying medicine.

46. The apparatus as defined in claim 38 further comprising means for mixing a solution of post-treatment agent to said solution of stabilized protein spheres for post-production stabilization.

47. The apparatus as defined in claim 38 further comprising means for rinsing said large scale production system after using it to produce said product.

* * * * *